United States Patent
Carson et al.

(10) Patent No.: US 6,573,267 B2
(45) Date of Patent: Jun. 3, 2003

(54) USEFUL AROYL AMINOACYL PYRROLE COMPOUNDS

(75) Inventors: John R. Carson, Norristown, PA (US); Philip M. Pitis, North Wales, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/896,084

(22) Filed: Jun. 29, 2001

(65) Prior Publication Data

US 2002/0019436 A1 Feb. 14, 2002

Related U.S. Application Data

(60) Provisional application No. 60/215,272, filed on Jun. 30, 2000.

(51) Int. Cl.[7] .................. A61K 31/40; A61K 31/4439; C07D 207/335; C07D 401/06
(52) U.S. Cl. .............. 514/254.01; 514/227.8; 514/235.5; 514/326; 514/343; 514/397; 514/422; 514/423; 544/58.2; 544/58.5; 544/141; 544/372; 546/208; 546/279.1; 548/314.7; 548/518; 548/527; 548/539
(58) Field of Search ................ 544/372, 58.2, 544/58.5, 141; 546/279.1, 208; 548/527, 539, 314.7, 518; 514/254.01, 343, 326, 422, 423, 227.8, 235.5, 397

(56) References Cited

U.S. PATENT DOCUMENTS

| | | | |
|---|---|---|---|
| 5,332,736 A | * 7/1994 | Carmosin et al. | 514/235.5 |
| 5,418,236 A | 5/1995 | Carmosin et al. | 514/252 |
| 5,512,537 A | 4/1996 | Tsang | 504/287 |
| 5,760,007 A | 6/1998 | Shank et al. | 514/23 |
| 6,191,142 B1 | 2/2001 | Carson et al. | 514/307 |

FOREIGN PATENT DOCUMENTS

| | | |
|---|---|---|
| WO | WO98/07447 A1 | 2/1998 |
| WO | WO48584 A | 8/2000 |
| WO | PCT/US01/20747 | 6/2001 |

OTHER PUBLICATIONS

Nadin Attal, et al.., Effects of Gabapentin on the Different Components of Peripheral and Central Neuropathic Pain Syndromes: A Pilot Study; Fr. Eur. Neurol., 1998, 40(4), pp. 191–200.

Krall et al; Antieplileptic Drug : II. Anticonvulsant Drug Screening; ., Epilepsia, 19, 409–428 (1978).

Chaplan et al., Role of Voltage–Dependent Calcium Channel Subtypes in Experimental Tactile Allodynia, J. Pharmacol. Exp. Ther. 1994, 269, pp 1117–1123.

Chung et al.,An Experimental model for peripheral neuropathy produced by segmental spinal nerve ligation in the rat, Pain, 1992, 50, pp 355–363.

J.R. CARSON ET AL., "Aroyl(aminoacyl)pyrroles, a New Class of Anticonvulsant Agents", Journal of Medicinal Chemistry, vol. 40, no. 11, 1997, pp. 1578–1584.

* cited by examiner

*Primary Examiner*—Richard L. Raymond
(74) *Attorney, Agent, or Firm*—John W. Harbour

(57) ABSTRACT

This invention is directed to aroyl aminoacyl pyrroles pharmaceutically useful as agents and modulators for the treatment of central nervous system disorders and a method for the treatment of central nervous system disorders including, but not limited to, use of the compounds of the present invention as anticonvulsant agents and modulators, antiepileptic agents and modulators, neuroprotective agents and modulators, muscle relaxant agents and modulators and as agents and modulators for the treatment of neuropathic pain.

6 Claims, No Drawings

USEFUL AROYL AMINOACYL PYRROLE COMPOUNDS

This application claims the benefit of U.S. Provisional Application No. 60/215,272, filed Jun. 30, 2000.

FIELD OF THE INVENTION

This invention relates to compounds useful as agents for the treatment of central nervous system disorders. More particularly, this invention relates to aroyl aminoacyl pyrrole compounds useful as agents for the treatment of central nervous system disorders including, but not limited to, epilepsy and neuropathic pain and methods for the treatment thereof.

BACKGROUND OF THE INVENTION

The conditions grouped under the term "central nervous system disorder" constitute an area of continuing medical need. Such conditions include those disorders associated with convulsions, epilepsy, neuroprotective diseases, muscle tension and neuropathic pain.

Epilepsy continues to be an area of development for new drugs and therapies. The structures of newer anticonvulsants has been summarized in Drugs of the Future, 1991, (16) 317–320. However, the impact of such drugs and therapies have yet to be fully evaluated.

Neuropathic pain is defined as pain caused by aberrant somatosensory processing in the peripheral or central nervous system. Chronic or debilitating conditions, such as post-herpetic neuralgia and phantom limb syndrome, are categorized as neuropathic pain.

Central nervous system disorders are widespread and cause pain and suffering. Moreover, current methods of treating such disorders are often inadequate.

Anticonvulsants have been suggested for the treatment of neuropathic pain. Nadin Attal, et al., Effects of Gabapentin on the Different Components of Peripheral and Central Neuropathic Pain Syndromes: A Pilot Study, *Fr. Eur. Neurol.* 1998, 40(4), 191–200 describes the anticonvulsant gabapentin having the following formula:

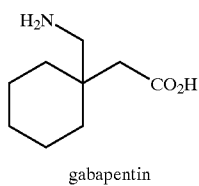

gabapentin

U.S. Pat. No. 5,760,007 describes other anticonvulsants useful in the treatment of neuropathic pain. More particularly, the reference describes the use of the anticonvulsant topiramate in treating neuropathic pain, wherein topiramate has the following general formula:

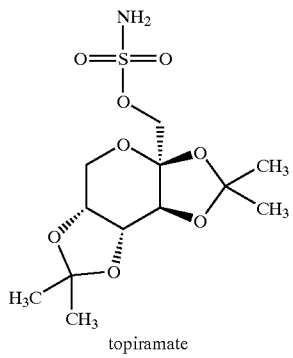

topiramate

Also, WO 98/07447 describes compositions combining an anticonvulsant and a non-toxic NMDA (N-methyl-D-aspartate) antagonist for use in neuropathic pain. Anticonvulsants suitable for use in the described combination include lamotrigine, gabapentin, valproic acid, topiramate, famotidine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan.

U.S. Pat. No. 5,332,736 to Carmosin, et al, describes other aroyl aminoacyl pyrrole compounds as useful anticonvulsants. The aroyl pyrrole compounds of the present invention, however, have not been previously described as useful agents for the treatment of central nervous system disorders.

Accordingly, it is an object of the present invention to provide aroyl pyrrole compounds useful as agents for the treatment of central nervous system disorders. It is also an object of the present invention to teach a method for the treatment of central nervous system disorders using the aroyl pyrrole compounds of the present invention including, but not limited to, their use as anticonvulsants, antiepileptics, neuroprotective agents, muscle relaxants and agents for the treatment of neuropathic pain.

SUMMARY OF THE INVENTION

The present invention provides aroyl aminoacyl pyrrole compounds as agents for the treatment of central nervous system disorders having Formula (I) and Formula (II):

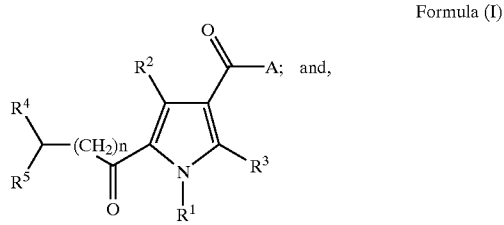

Formula (I)

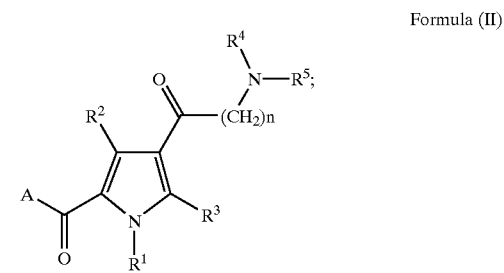

Formula (II)

wherein
A is a substituent selected from the group consisting of aryl and heteroaryl optionally substituted with one to two substituents selected from the group consisting of halogen, $C_{1-8}$alkyl, $C_{1-8}$alkoxy, tri(halogen)$C_{1-8}$alkyl and tri(halogen)$C_{1-8}$alkoxy;

n is an integer from 1 to 5;

$R^1$ is $C_{1-8}$alkyl optionally substituted with one to two substituents independently selected from the group consisting of hydroxy, $C_{1-8}$alkoxy (optionally substituted with —S$C_{1-8}$alkyl), $C_{1-8}$acyl, carboxy, carbonyl (further substituted with $C_{1-8}$alkyl, $C_{1-8}$alkoxy, amino or —S$C_{1-8}$alkyl), oxy (further substituted with carbonyl$C_{1-8}$alkyl, carbonyl$C_{1-8}$alkoxy or carbonylamino), amino (optionally further substituted with one or two substituents independently selected from $C_{1-8}$alkyl, $C_{1-8}$acyl, carbonyl$C_{1-8}$alkyl, carbonyl$C_{1-8}$alkoxy, sulfinyl$C_{1-8}$alkyl or sulfonyl$C_{1-8}$alkyl), ureido (optionally further substituted with $C_{1-8}$alkyl), thio (optionally further substituted with $C_{1-8}$alkyl or amino), sulfinyl (optionally further substituted with $C_{1-8}$alkyl or amino) and sulfonyl (optionally further substituted with $C_{1-8}$alkyl or amino);

$R^2$ and $R^3$ are substituents independently selected from the group consisting of hydrogen and $C_{1-8}$alkyl;

$R^4$ and $R^5$ are substituents independently selected from the group consisting of hydrogen, $C_{1-8}$alkyl and aryl$C_{1-8}$alkyl; wherein aryl is optionally substituted with one to three substituents selected from the group consisting of $C_{1-8}$alkyl, $C_{1-8}$alkoxy, tri(halo)$C_{1-8}$alkyl and tri(halo)$C_{1-8}$alkoxy;

or, in the alternative, $R^4$ and $R^5$ may be fused together with nitrogen to form a heterocyclic ring selected from the group consisting of:

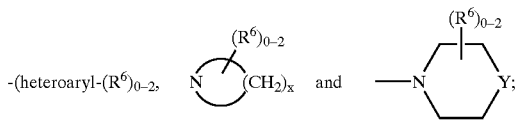

wherein x is an integer from 3 to 7 and Y is selected from the group consisting of N, S, S=O, $SO_2$ and 0; and $R^6$ is a substituent selected from the group consisting of $C_{1-8}$alkyl and hydroxy$C_{1-8}$alkyl;

and pharmaceutically acceptable acid addition salts thereof; with the proviso that, in the case of compound wherein:

wherein n is an integer from 1 to 5; $R^1$ is selected from the group consisting of hydrogen and $C_{1-4}$alkyl; $R^2$ and $R^3$ are selected from the group consisting of hydrogen and $C_{1-4}$alkyl; $R^4$ and $R^5$ are independently selected from the group consisting of hydrogen, $C_{1-4}$alkyl, phenyl$C_{1-4}$alkyl and substituted phenyl$C_{1-4}$alkyl where the substituent is on phenyl and selected from the group consisting of methyl and methoxy; or in the alternative, are fused and together with the nitrogen form a heterocyclic ring selected from the group consisting of: 4-[bis(4-fluorophenyl)methylene]-piperidin-1-yl, 1,2,3,4-tetrahydro-6,7-dimethoxy-isoquinolin-2-yl,

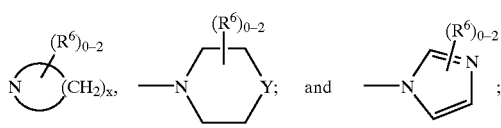

wherein Y is S or O and x is 3 to 7; and, $R^6$ is selected from the group consisting of methyl and hydroxymethyl; then, A cannot be substituted or unsubstituted phenyl.

The present invention also provides a method for the treatment of central nervous system disorders comprising the step of administering to a mammal suffering from such condition a therapeutically effective amount of an active compound selected from Formula (I) and Formula (II).

DETAILED DESCRIPTION OF THE INVENTION

Relative to the above generic description, certain compounds of Formula (I) and Formula (II) are preferred. Preferred embodiments are those compounds wherein A is a substituent selected from the group consisting of phenyl, naphthalenyl, furyl, thienyl, pyrrolyl, pyrrolinyl, oxazolyl, thiazolyl, imidazolyl, imidazolinyl, pyrazolyl, pyrazolinyl, isoxazolyl, isothiazolyl, pyridinyl, pyridazinyl, pyrimidinyl, pyrazinyl or quinolinyl optionally mono- or di-substituted with chlorine, methyl, ethyl, methoxy, trifluoromethyl or trifluoromethoxy. More preferably, A is selected from phenyl, naphthalenyl, thienyl or pyridinyl optionally mono- or di-substituted with chlorine, methyl or methoxy.

n is an integer from 1 to 2.

$R^1$ is $C_{1-8}$alkyl optionally substituted with one to two substituents independently selected from the group consisting of $C_{1-8}$alkoxy and amino; wherein amino is optionally substituted with one to two substituents independently selected from $C_{1-8}$alkyl. More preferably, $R^1$ is a substituent selected from the group consisting of methyl, ethyl, n-propyl, n-butyl and t-butyl optionally substituted with one to two substituents independently selected from the group consisting of methoxy, ethoxy, propoxy and amino; wherein amino is optionally substituted with one to two substituents independently selected from methyl, ethyl, n-propyl, n-butyl and t-butyl. Most preferably, $R^1$ is a substituent selected from the group consisting of methyl, ethyl and n-propyl optionally substituted with one to two substituents independently selected from the group consisting of methoxy, ethoxy and amino; wherein amino is optionally substituted with one to two substituents independently selected from the group consisting of methyl and ethyl.

$R^2$ and $R^3$ are substituents independently selected from the group consisting of hydrogen, methyl, ethyl and propyl. More preferably, $R^2$ and $R^3$ are substituents independently selected from the group consisting of hydrogen and methyl.

$R^4$ and $R^5$ are substituents independently selected from the group consisting of hydrogen, methyl, ethyl, propyl, n-butyl, benzyl, phenethyl and phenylpropyl; wherein phenyl is optionally substituted with one to three substituents selected from the group consisting of methyl, ethyl, propyl, methoxy, ethoxy, propoxy, trifluoromethyl and trifluoromethoxy. More preferably, $R^4$ and $R^5$ are substituents independently selected from the group consisting of methyl, ethyl, propyl, benzyl, phenethyl and phenylpropyl; wherein phenyl is optionally substituted with one to three substituents selected from the group consisting of methyl, ethyl, methoxy and ethoxy. Most preferably, $R^4$ and $R^5$ are substituents independently selected from the group consisting of methyl, ethyl and propyl.

Alternatively, $R^4$ and $R^5$ may be fused together with nitrogen to form a substituent selected from the group consisting of pyrrolidinyl, piperidinyl, morpholinyl, thiomorpholinyl, 1-oxidethiomorpholinyl, 1,1-dioxidethiomorpholinyl, piperazinyl and imidazolyl optionally substituted with a substituent selected from $R^6$. More preferably, $R^4$ and $R^5$ may be fused together with nitrogen to form a substituent selected from the group consisting of piperidinyl, morpholinyl, thiomorpholinyl, piperazinyl and imidazolyl optionally substituted with a substituent selected from $R^6$. Most preferably, $R^4$ and $R^5$ may be fused together with nitrogen to form a substituent selected from the group consisting of piperidinyl, piperazinyl and imidazolyl optionally substituted with a substituent selected from $R^6$.

$R^6$ is a substituent selected from the group consisting of methyl, ethyl, propyl, n-butyl, hydroxymethyl, 1-hydroxyethyl and 1-hydroxypropyl. More preferably, $R^6$ is a substituent selected from the group consisting of methyl, ethyl, hydroxymethyl and 1-hydroxyethyl. Most preferably, $R^6$ is methyl.

Exemplifying the invention is a compound of Formula (I) and Formula (II) selected from:

| Cpd | Compound Name |
|---|---|
| 1 | 1-[4-(2-Naphthalenoyl)-1-methyl-1H-pyrrol-2-yl]-2-(N,N-diethylamino)ethanone |
| 2 | 1-[4-(2-Thienoyl)-1-methyl-1H-pyrrol-2-yl]-2-(N,N-diethylamino)ethanone |
| 3 | 1-[4-(1-Naphthalenoyl)-1-methyl-1H-pyrrol-2-yl]-2-(N,N-diethylamino)ethanone |
| 4 | 1-[4-(1-Naphthalenoyl)-1-methyl-1H-pyrrol-2-yl]-2-(1-piperidinyl)ethanone |
| 5 | 1-[4-(2-Naphthalenoyl)-1-(N,N-dimethylaminoeth-2-yl)-1H-pyrrol-2-yl]-2-(1-piperidinyl)ethanone |
| 6 | 1-[5-(5-Chlorothieno-2-yl)-1-methyl-1H-pyrrol-3-yl]-2-(N,N-diethylamino)ethanone |
| 7 | 1-[5-(4-Chlorobenzoyl)-1-methyl-1H-pyrrol-3-yl]-2-(4-methyl-1-piperazinyl)ethanone |
| 8 | 1-[5-(1-Naphthalenoyl)-1-methyl-1H-pyrrol-3-yl]-3-(1-piperidinyl)-1-propanone |
| 9 | 1-[5-(4-Chlorobenzoyl)-1-ethylmethoxy-1H-pyrrol-3-yl]-2-[N,N-diethylamino]ethanone |
| 10 | 1-[5-(2-Thienoyl)-1-methyl-1H-pyrrol-3-yl]-2-(N,N-diethylamino)ethanone |
| 11 | 1-[5-(2-Thienoyl)-1-methyl-1H-pyrrol-3-yl]-2-(1-piperidinyl)ethanone |
| 12 | 1-[5-(3-Pyridinoyl)-1-methyl-1H-pyrrol-3-yl]-2-(N,N-diethylamino)ethanone |
| 13 | 1-[5-(2-Naphthalenoyl)-1-methyl-1H-pyrrol-3-yl]-2-(N,N-diethylamino)ethanone |
| 14 | 1-[5-(4-Chlorobenzoyl)-1-(N,N-dimethylaminoprop-3-yl)-1H-pyrrol-3-yl]-2-(1-piperidinyl)ethanone |
| 15 | 1-[5-(2-Naphthalenoyl)-1-methyl-1H-pyrrol-3-yl]-2-(N,N-ethylmethylamine)ethanone |
| 16 | 1-[5-(2-Chlorobenzoyl)-1-ethylthiomethyl-1H-pyrrol-3-yl]-2-(N,N-diethylamino)ethanone |
| 17 | 1-[4-(2-Naphthalenoyl)-1-methyl-1H-pyrrol-2-yl]-2-(1-piperidinyl)ethanone |
| 18 | 1-[4-(5-Chloro-2-thienoyl)-1-methyl-1H-pyrrol-2-yl]-2-(1-piperidinyl)ethanone |

Table 1 lists particular compounds of the present invention having Formula (I)

TABLE 1

Formula (I)
wherein n, A, $R^1$, $R^2$, $R^3$, $R^4$ and $R^5$ are selected from

| Cpd | n | A | $R^1$ | $R^2/R^3$ | $R^4/R^5$ |
|---|---|---|---|---|---|
| 1 | 1 | 2-naphthalenyl | $CH_3$ | H/H | $CH_2CH_3/CH_2CH_3$ |
| 2 | 1 | 2-thienyl | $CH_3$ | H/H | $CH_2CH_3/CH_2CH_3$ |
| 3 | 1 | 1-naphthalenyl | $CH_3$ | H/H | $CH_2CH_3/CH_2CH_3$ |
| 4 | 1 | 1-naphthalenyl | $CH_3$ | H/H | 1-piperidinyl |
| 5 | 1 | 2-naphthalenyl | $(CH_2)_2N(CH_3)_2$ | H/H | 1-piperidinyl |
| 17 | 1 | 2-naphthalenyl | $CH_3$ | H/H | 1-piperidinyl |
| 18 | 1 | 2-(5-Cl)thienyl | $CH_3$ | H/H | 1-piperidinyl |

Table 2 lists particular compounds of the present invention having Formula (II)

TABLE 2

Formula (II)
wherein n, A, $R^1$, $R^2$, $R^3$, $R^4$ and $R^5$ are selected from

| Cpd | n | A | $R^1$ | $R^2/R^3$ | $R^4/R^5$ |
|---|---|---|---|---|---|
| 6 | 1 | 2-(5-Cl)thienyl | $CH_3$ | H/H | $CH_2CH_3/CH_2CH_3$ |
| 7 | 1 | 4-Cl—Ph | $CH_3$ | H/H | 4-$CH_3$-1-piperazinyl |
| 8 | 2 | 1-naphthalenyl | $CH_3$ | H/H | 1-piperidinyl |
| 9 | 1 | 4-Cl—Ph | $(CH_2)_2OCH_3$ | H/H | $CH_2CH_3/CH_2CH_3$ |
| 10 | 1 | 2-thienyl | $CH_3$ | H/H | $CH_2CH_3/CH_2CH_3$ |
| 11 | 1 | 2-thienyl | $CH_3$ | H/H | 1-piperidinyl |
| 12 | 1 | 3-pyridinyl | $CH_3$ | H/H | $CH_2CH_3/CH_2CH_3$ |
| 13 | 1 | 2-naphthalenyl | $CH_3$ | H/H | $CH_2CH_3/CH_2CH_3$ |
| 14 | 1 | 4-Cl—Ph | $(CH_2)_3N(CH_3)_2$ | H/H | 1-piperidinyl |
| 15 | 1 | 2-naphthalenyl | $CH_3$ | H/H | $CH_3/CH_2CH_3$ |
| 16 | 1 | 2-Cl—Ph | $(CH_2)_2SCH_3$ | H/H | $CH_2CH_3/CH_2CH_3$ |

Particularly preferred compounds having Formula (I) and Formula (II) for as anticonvulsant agents include

| Cpd | Compound Name |
|---|---|
| 1 | 1-[4-(2-Naphthalenoyl)-1-methyl-1H-pyrrol-2-yl]-2-(N,N-diethylamino)ethanone |
| 2 | 1-[4-(2-Thienoyl)-1-methyl-1H-pyrrol-2-yl]-2-(N,N-diethylamino)ethanone |
| 3 | 1-[4-(1-Naphthalenoyl)-1-methyl-1H-pyrrol-2-yl]-2-(N,N-diethylamino)ethanone |
| 4 | 1-[4-(1-Naphthalenoyl)-1-methyl-1H-pyrrol-2-yl]-2-(1-piperidinyl)ethanone |
| 6 | 1-[5-(5-Chlorothieno-2-yl)-1-methyl-1H-pyrrol-3-yl]-2-(N,N-diethylamino)ethanone |
| 7 | 1-[5-(4-Chlorobenzoyl)-1-methyl-1H-pyrrol-3-yl]-2-(4-methyl-1-piperazinyl)ethanone |
| 8 | 1-[5-(1-Naphthalenoyl)-1-methyl-1H-pyrrol-3-yl]-3-(1-piperidinyl)-1-propanone |
| 11 | 1-[5-(2-Thienoyl)-1-methyl-1H-pyrrol-3-yl]-2-(1-piperidinyl)ethanone |
| 15 | 1-[5-(2-Naphthalenoyl)-1-methyl-1H-pyrrol-3-yl]-2-(N,N-ethylmethylamine)ethanone |

Particularly preferred compounds having Formula (I) and Formula (II) for use as agents for the treatment of neuropathic pain include

| Cpd | Compound Name |
|---|---|
| 1 | 1-[4-(2-Naphthalenoyl)-1-methyl-1H-pyrrol-2-yl]-2-(N,N-diethylamino)ethanone |
| 3 | 1-[4-(1-Naphthalenoyl)-1-methyl-1H-pyrrol-2-yl]-2-(N,N-diethylamino)ethanone |
| 6 | 1-[5-(5-Chlorothieno-2-yl)-1-methyl-1H-pyrrol-3-yl]-2-(N,N-diethylamino)ethanone |
| 13 | 1-[5-(2-Naphthalenoyl)-1-methyl-1H-pyrrol-3-yl]-2-(N,N-diethylamino)ethanone |

| Cpd | Compound Name |
|---|---|
| 14 | 1-[5-(4-Chlorobenzoyl)-1-(N,N-dimethylaminoprop-3-yl)-1H-pyrrol-3-yl]-2-(1-piperidinyl)ethanone |

Particularly preferred compounds having Formula (I) and Formula (II) for use as both anticonvulsant modulators and modulators for the treatment of neuropathic pain include

| Cpd | Compound Name |
|---|---|
| 1 | 1-[4-(2-Naphthalenoyl)-1-methyl-1H-pyrrol-2-yl]-2-(N,N-diethylamino)ethanone |
| 3 | 1-[4-(1-Naphthalenoyl)-1-methyl-1H-pyrrol-2-yl]-2-(N,N-diethylamino)ethanone |
| 6 | 1-[5-(5-Chlorothieno-2-yl)-1-methyl-1H-pyrrol-3-yl]-2-(N,N-diethylamino)ethanone |

The terms used in describing the invention are commonly used and known to those skilled in the art. As used herein, the following abbreviations have the indicated meanings:

| | |
|---|---|
| DCE | 1,2-dichloroethane |
| $Et_2O$ | Diethyl ether |
| EtOH | Ethanol |
| h | Hour |
| $K_2CO_3$ | Potassium carbonate |
| MeOH | Methanol |
| $NaBH_4$ | Sodium borohydride |
| $NaBH(OAc)_3$ | Sodium triacetoxyborohydride |
| min | Minute |
| 2-PrOH | 2-Propanol |
| rt | Room Temperature |
| $TiCl_4$ | Titanium(IV) tetrachloride |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

Instant compounds useful as agents for the treatment of central nervous system disorders may be placed into two categories, those having an aromatic ring at the 2-carbonyl position and those having an aromatic ring at the 4-carbonyl position. Both categories of compounds may be prepared by variations of what is fundamentally the same reaction scheme.

Scheme A exemplifies the preparation of compounds having an aromatic ring at the 2-position. Referring to Scheme A, in the first step a simple pyrrole Compound A1 is acylated with an appropriately substituted aroyl chloride Compound A2 to produce aroyl pyrrole Compound A3. This acylation may be carried out by simply heating the aroyl chloride and the pyrrole in an aprotic solvent followed by removing excess aroyl chloride by reaction with a dibasic amine and extraction with HCl.

The temperature of the acylation will vary depending upon the desired rate of reaction and the substituents of pyrrole Compound A1. Preferably the acylation is carried out at a temperature of from 50 to 250° C. A suitable dibasic amine is dimethyl-3-aminopropyl amine. In the case where $R^1$ is hydrogen the acylation, as described, may not produce desirable yields. In this case, a Vilsmeier type acylation as employed by J. White and G. McGillivrey, J. Org. Chem., Vol. 42, pp 42–48, 1977 might be expeditiously employed.

Subsequently, the aroyl pyrrole Compound A3 is acylated at the 4-position in a Friedel-Crafts reaction with the halogenated acid chloride Compound A4 to produce a 2-aroyl-4-halogenated alkanoyl pyrrole Compound A5. The Friedel-Crafts reaction is carried out by refluxing the halogenated carboxylic acid chloride Compound A4, in which X is Cl, Br or 1, with product Compound A3 in a solvent with a Friedel-Crafts reagent followed by treatment with HCl and evaporation of the solvent. Suitable Friedel-Crafts reagents include aluminum chloride, zinc chloride, BF3 or $TiCl_4$. Suitable solvents include methylene chloride, 1,2-dichloroethane, carbon tetrachloride or chloroform. The temperature of reflux might vary between 30 and 150° C.

To produce Compound A7, the 2-aroyl-4-halogenated alkanoyl pyrrole Compound A5 is aminated with amine Compound A6 to produce the desired 2-aroyl-4-aminoalkanoyl pyrrole Compound A7. The amination may be carried out by heating the reactants Compound A5 and Compound A6 neat or in a solvent to a temperature of from 40 to 120° C. and preferably from 50 to 90° C. Suitable solvents, where employed, include ethanol, 1-propanol or toluene.

Scheme B exemplifies the preparation of compounds having an aromatic ring at the 4-position. Except for the specifics of the reactants, each step of Scheme B is analogous to the corresponding step of Scheme A with the reactions and description thereof being identical. Referring to Scheme B, in the first step a simple pyrrole Compound B1 is acylated with an appropriately substituted halogenated alkanoyl chloride Compound B2 to produce halogenated alkanoyl pyrrole Compound B3. Subsequently, alkanoyl pyrrole Compound B3 is acylated at the 4-position in a Friedel-Crafts reaction with aroyl acid chloride Compound B4 to produce 2-halogenated alkanoyl-4-aroyl pyrrole Compound B5. In the third reaction, 2-halogenated alkanoyl-4-aroyl pyrrole Compound B5 is aminated with amine Compound B6 to produce the desired 2-aminoalkanoyl-4-aroyl pyrrole Compound B7.

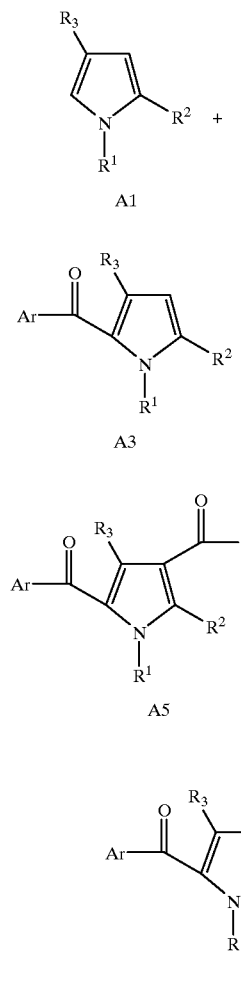

SCHEME A

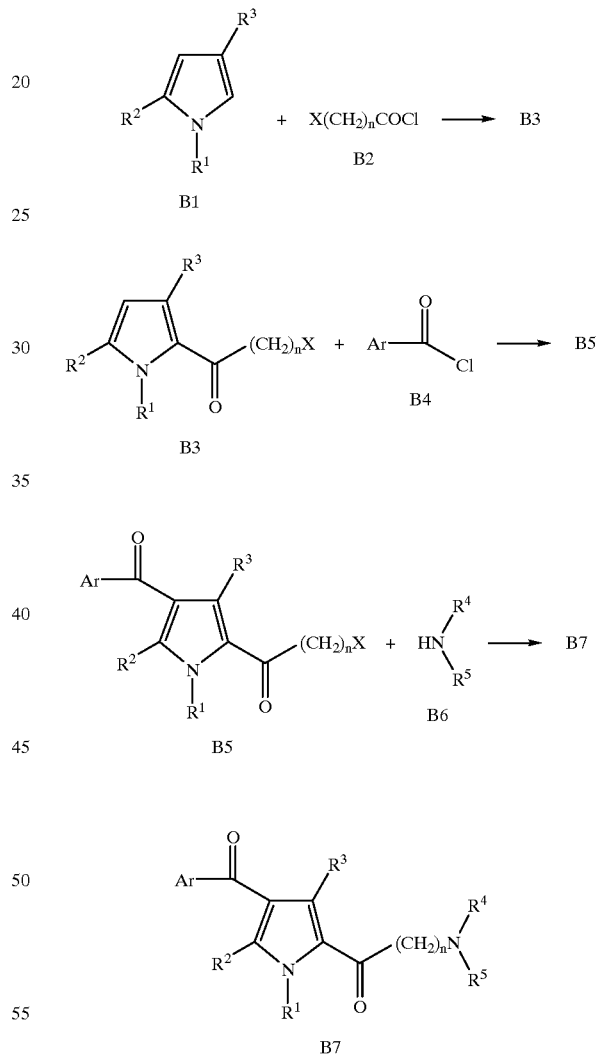

SCHEME B

Scheme C exemplifies the preparation of compounds wherein $R^1$ is substituted with substituents other than methyl and the aromatic ring is at the 2-position. Referring to Scheme C in the first step a simple pyrrole Compound C1 is acylated with (dimethylamino)benzamide C2 to produce benzoyl pyrrole C3. This was accomplished by means of a Vilsmeyer reaction. Subsequent steps are identical to Scheme A through Compound C7. Compound C7 was alkylated with the appropriate haloalkyl Compound C8 in the presence of base to give Compound C9.

SCHEME C

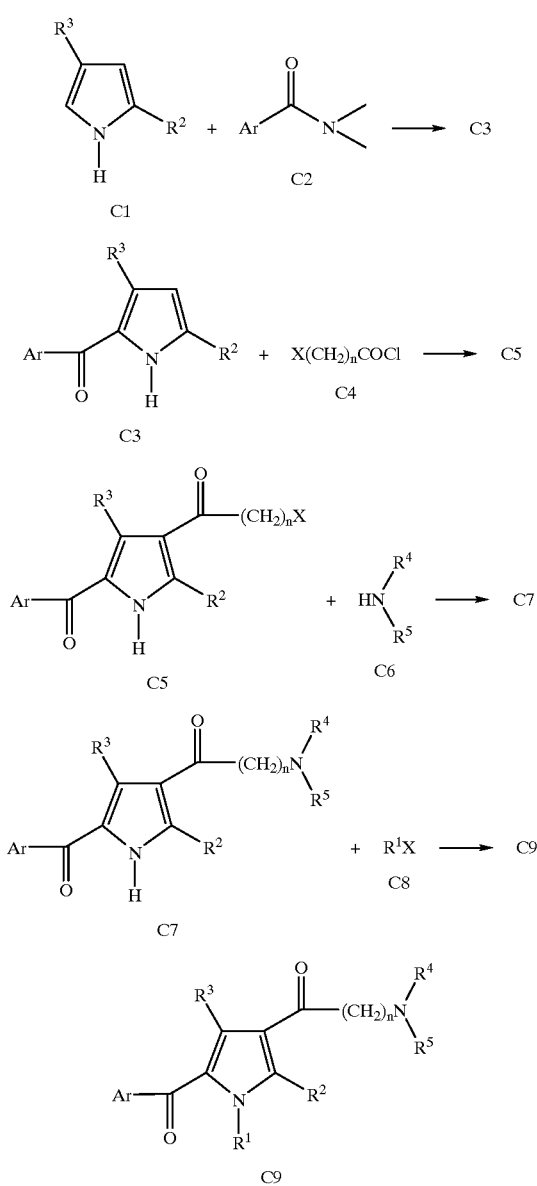

Scheme D was identical to Scheme C with the exception of reversing the order of steps 3 and 4.

SCHEME D

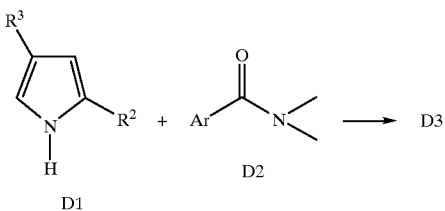

The compounds herein readily form pharmaceutically acceptable acid addition salts. Such salts include hydrochlorides, sulfates, phosphates, methane sulfonates, fumarates, maleates, citrates, lactates, and the like. Those skilled in the art will readily recognize suitable methods for manufacture and use of the acid addition salts.

Specific Synthetic Methods

Specific compounds which are representative of this invention may be prepared as per the following examples offered by way of illustration and not by way of limitation. Also, examples specifically used to prepare intermediates for the further synthesis of compounds of the invention are designated by "Procedure." No attempt has been made to optimize the yields obtained in any of the reactions. One skilled in the art would know how to increase such yields through routine variations in reaction times, temperatures, solvents and/or reagents.

Procedure 1

(2-Naphthalenyl)(1-methyl-1H-pyrrol-2-yl) methanone

N-Methylpyrrole (19.5 g, 0.24 mole) and 2-napthalenoyl chloride (50.0 g, 0.26 mole) 300 mL of dry toluene were heated under reflux overnight with a nitrogen stream bubbling through the reaction mixture. Another 10 mL of N-methylpyrrole was added to the reaction mixture and the reflux was continued for another 38 hr. 100 mL of 20% aqueous 3-(dimethylamino)propylamine was added and stirred for 30 minutes. Et$_2$O/THF was added and the organics were separated off, washed with 1 N HCl, NaHCO$_3$, water, brine and dried (MgSO$_4$). The solvent was evaporated in vacuo to give 51 g (90%) of (2-naphthalenyl)(1-methyl-1H-pyrrol-2-yl)-methanone. mp 108–110° C. CIMS m/z236 (MH$^+$). $^1$H NMR (300 MHz, CDCl$_3$) δ 8.35 (Ar, 1H); 8.0–7.9 (Ar, 4H); 7.6–7.5 (Ar, 2H); 6.95 (Ar, 1H); 6.8 (Ar, 1H); 6.2 (Ar, 1H); 4.1 (s, 3H).

Using the method of Procedure 1, substituting the correct acid chloride for the 2-naphthalenoyl chloride, the following compounds were prepared:

(2-Thienyl)(1-methyl-1H-pyrrol-2-yl)methanone
(oil) CIMS m/z 192 (MH$^+$). $^1$H NMR (300 MHz, CDCl$_3$) δ 7.75 (Ar, 1H); 7.6 (Ar, 1H); 7.1 (Ar, 1H); 7.0 (Ar, 1H); 6.9 (Ar, 1H); 6.2 (Ar, 1H); 4.0 (s, 3H).

(5-Chlorothien-2-yl)(1-methyl-1H-pyrrol-2-yl)methanone
(oil) CIMS m/z 226 (MH$^+$).

Procedure 2

2-Chloro-1-[5-(2-naphthalenoyl)-1-methyl-1H-pyrrol-3-yl]ethanone

A 71 g (0.44 mole) sample of aluminum chloride was added in portions over 15 minutes to 51 g (0.217 mole) of (2-naphthalenyl)(1-methyl-1H-pyrrol-2-yl)methanone in 500 mL of 1,2-dichloroethane (DCE) at 5° C. After stirring for 15 minutes, a solution of 32 mL (0.44 mole) of chloroacetyl chloride in 50 mL 1,2-DCE was added dropwise. After stirring for 30 minutes, the ice bath was removed and stirred for 3 hr. The reaction mixture was poured into ice/3N HCl. The organics were washed with water, NaHCO3, water, brine, and dried (Na$_2$SO$_4$). The solvent was evaporated in vacuo and the residue recrystallized from EtOAc to give 41.2 g (61%) of 2-chloro-1-[4-(2-naphthalenoyl)-1-methyl-1H-pyrrol-2-yl]ethanone. mp 148–151° C. CIMS m/z 312 (MH$^+$). $^1$H NMR (300 MHz, CDCl$_3$) δ 8.35 (s, 1H); 8.1–7.85 (Ar, 4H); 7.6 (Ar, 3H); 7.2 (Ar, 2H); 4.4 (s, 2H); 4.05 (s, 3H).

Using the method of Procedure 2, the following compounds were prepared:

2-Chloro-1-[4-(2-thienoyl)-1-methyl-1H-pyrrol-2-yl]ethanone
mp 134–136° C. CIMS m/z 267 (MH$^+$). Anal calc'd for: C$_{12}$H$_{10}$ClNO$_2$S: C, 53.83; H, 3.76; N, 5.23. Found: C, 53.67; H, 3.94; N, 5.19.

2-Chloro-1-[4-(5-chlorothieno-2-yl)-1-methyl-1H-pyrrol-2-yl]ethanone
mp 110–112° C. CIMS m/z 303 (MH$^+$). $^1$H NMR (300 MHz, CDCl$_3$) δ 8.1 (s, 1H); 7.8 (Ar, 1H); 7.5 (Ar, 1H); 7.3 (Ar, 1H); 4.9 (s, 2H); 3.9 (s, 3H).

2-Chloro-1-[4-(2-pyridinoyl)-1-methyl-1H-pyrrol-2-yl]ethanone
By the method of procedure 2 using the hydrochloride salt of (2-pyridinyl)(1-methyl-1H-pyrrol-2-yl)methanone. CIMS m/z 263 (MH$^+$).

EXAMPLE 1

1-[4-(2-Naphthalenoyl)-1-methyl-1H-pyrrol-2-yl]-2-(N,N-diethylamino)ethanone (Compound 1)
A solution of 2.5 g (0.008 mole) of 2-chloro-1-[4(2-naphthalenoyl)-1-methyl-1H-pyrrol-2-yl]ethanone and 2.5 mL (0.024 mole) of diethylamine was refluxed for 3 hr in 50 mL of EtOH. After cooling, the solvent was evaporated in vacuo. The residue was chromatographed on silica gel (90:10:1 CH$_2$Cl$_2$:MeOH:NH$_4$OH). The resulting oil was treated with ethereal HCl in EtOH. The resulting gum was converted to the free base by partitioning between Et$_2$O/NaHCO$_3$. This was again chromatographed on silica gel (90:10:1 CH$_2$Cl$_2$:MeOH:NH$_4$OH). The resulting oil was converted to the fumarate salt in 2-PrOH/EtOH. The solid was filtered to give 0.76 g (27%) of Compound 1. mp 130–132° C. CIMS m/z=349 (MH$^+$). $^1$H NMR (300 MHz, CDCl$_3$) δ 8.4 (Ar, 1H); 8.15–8.0 (Ar, 4H); 7.85 (Ar, 1H); 7.7–7.6 (Ar, 2H); 7.2 (Ar, 1H); 6.6 (s, 2H); 4.0 (s, 3H); 3.7 (s, 2H); 2.6 (q, 4H); 1.0 (t, 6H). Anal calc'd for: C$_{22}$H$_{24}$N$_2$O$_2$.C$_4$H$_4$O$_4$0.33H$_2$O: C, 66.40; H, 6.14; N, 5.96. Found: C, 66.38; H, 6.43; N, 5.73, KF water 1.22.

Using the method of Example 1 and the appropriate ethanone and amine in either EtOH or 2-PrOH, respectively, the following compounds were prepared:

EXAMPLE 2

1-[5-(2-Thienoyl)-1-methyl-1H-pyrrol-3-yl]-2-(N,N-diethylamino)ethanone (Compound 10)
mp 153–155° C. CIMS m/z 305 (MH$^+$). $^1$H NMR (300 MHz, DMSO-d$_6$) δ 8.1 (Ar, 2H); 7.9 (Ar, 1H); 7.5 (Ar, 1H); 7.3 (Ar, 1H); 6.6 (s, 2.5H); 4.0 (s, 3H); 3.85 (s, 2H); 2.7 (q, 4H); 1.0 (t, 6H). Anal calc'd for: C$_{16}$H$_{20}$N$_2$O$_2$S. 1.25 C$_4$H$_4$O$_4$: C, 56.11; H, 5.61; N, 6.23. Found: C, 56.01; H, 5.74; N, 6.17.

EXAMPLE 3

1-[5-(2-Thienoyl)-1-methyl-1H-pyrrol-3-yl]-2-(1-piperidinyl)ethanone (Compound 11)
mp. 178–179° C. CIMS m/z 317 (MH$^+$). $^1$H NMR (300 MHz, DMSO-d$_6$) δ 8.1 (Ar, 2H); 7.9 (Ar, 1H); 7.5 (s, 1H); 7.3 (Ar, 1H); 6.6 (s, 3H); 3.95 (s, 3H); 3.7 (s, 2H); 2.6 (m, 4H); 1.6 (m, 4H); 1.4 (m, 2H).

EXAMPLE 4

1-[5-(5-Chlorothieno-2-yl)-1-methyl-1H-pyrrol-3-yl]-2-(N,N-diethylamino)ethanone (Compound 6)
mp 187.5–188° C. CIMS m/z 339 (MH$^+$). $^1$H NMR (300 MHz, DMSO-d$_6$) δ 8.2 (s, 1H); 7.85 (Ar, 1H); 7.6 (Ar, 1H); 7.4 (Ar, 1H); 4.7 (d, 2H); 3.9 (s, 3H); 3.1 (q, 4H); 1.15 (t, 6H). Anal calc'd for C$_{16}$H$_{19}$N$_2$O$_2$S.HCl: Theory: C, 51.20; H, 5.37; N, 7.46. Found: C, 51.06; H, 5.31; N, 7.14.

EXAMPLE 5

1-[5-(3-Pyridinoyl)-1-methyl-1H-pyrrol-3-yl]-2-(N,N-diethylamino)ethanone (Compound 12)
mp 158–160(dec) ° C. CIMS m/z 300 (MH$^+$). $^1$H NMR (300 MHz, DMSO-d$_6$) δ 9.0 (Ar, 1H); 8.9 (Ar, 1H); 8.3 (Ar, 2H); 7.7 (Ar, 1H); 7.3 (Ar, 1H); 5.4 (bs, 1H); 4.7 (d, 2H); 4.0 (s, 3H); 3.2 (q, 4H); 1.2 (t, 6H). Anal calc'd for: C$_{17}$H$_{21}$N$_3$O$_2$0. 2HCl.0.65H$_2$O: Theory: C, 53.20; H, 6.38; N, 10.95. Found: C, 53.53; H, 6.33; N, 10.83. KF water 3.43.

EXAMPLE 6

1-[5-(2-Naphthalenoyl)-1-methyl-1H-pyrrol-3-yl]-2-(N,N-ethylmethylamine)ethanone (Compound 15)
mp 130–133° C. CIMS m/z 335 (MH$^+$). $^1$H NMR (300 MHz, DMSO-d$_6$) δ 8.4 (Ar, 1H); 8.25–8.05 (Ar, 4H); 7.9 (Ar, 1H); 7.7 (Ar, 2H); 7.25 (Ar, 1H); 4.7 (m, 2H); 4.05 (s, 3H); 3.4 (s, 5H); 1.2 (t, 3H).

Procedure 3

(2-Pyridinyl)(1-methyl-1H-pyrrol-2-yl)methanone
A mixture of 25 g (0.14 moles) of nicotinoyl chloride hydrochloride and 10.4 mL (0.14 mole) of N-methylpyrrole was heated under reflux in 200 mL of dry toluene while a nitrogen stream was bubbled slowly through the reaction mixture. After refluxing overnight the reaction mixture was cooled and the solid filtered off. The solid was converted the free base by partitioning between $Et_2O$/3N NaOH. The organics were washed with water, brine and dried ($K_2CO_3$). The residue was chromatographed on silica (90:10:1 $CH_2Cl_2$:MeOH:$NH_4OH$) to give 8.9 g of (2-pyridinyl)(1-methyl-1H-pyrrol-2-yl)-methanone (34%) as a gum. CIMS m/z 188 (MH+).$^1$H NMR (300 MHz, $CDCl_3$) δ 9.0 (Ar, 1H); 8.7 (Ar, 1H); 8.1 (Ar, 1H); 7.4 (Ar, 1H); 6.7 (Ar, 1H); 6.2 (Ar, 1H), 4.0 (s, 3H).

Procedure 4

2-[2-(1-Naphthalenoyl)-1-methyl-1H-pyrrol-4-yl] ethanone

A mixture 10 g (0.081 mole) of 3-acetyl-1-methylpyrrole, 24 mL (0.16 mole) of 1-naphthalenoyl chloride and 25 g (0.16 mole) of aluminum chloride in 100 mL of 1,2-dichloroethane was stirred for 4 h. The reaction mixture was poured into 2N HCl and ice. The organics were separated off, washed with water, $NaHCO_3$, water, brine and dried ($MgSO_4$). The solvent was evaporated in vacuo. The resulting residue was chromatographed on silica gel (4:1 hexane:acetone) to give 5.86 g (26%) of 2-[2-(1-naphthalenoyl)-(1-methyl-1H-pyrrol-4-yl)-2-ethanone. mp 123–125° C. $^1$H NMR (300 MHz, $CDCl_3$) δ 8.15 (Ar, 1H); 8.0 (Ar, 1H); 7.9 (Ar, 1H); 7.7 (Ar, 1H); 7.5 (Ar, 4H); 6.9 (Ar, 1H); 4.2 (s, 3H); 2.45 (s, 3H).

EXAMPLE 7

1-[5-(1-Naphthalenoyl)-1-methyl-1H-pyrrol-3-yl]-3-(1-piperidinyl)-1-propanone (Compound 8)

A solution of 2.5 g (0.005 moles) of 1-[5-(1-naphthalenoyl)(1-methyl-1H-pyrrol-3-yl)]-1-ethanone, 1.1 g (0.0065 mole) of piperidine hydrochloride, and 1.0 g (0.0065 mole) paraformaldehyde in 50 mL of MeOH was heated at 65° C. for 48 h and stirred 72 h at room temperature, the reaction mixture was poured into 3N NaOH and extracted with $Et_2O$. The organics were washed with water, brine and dried ($Na_2SO_4$). The solvent was evaporated in vacuo and the residue chromatographed on silica gel (95:5:0.5 $CH_2Cl_2$:MeOH:$NH_4OH$). The resulting oil was treated with ethereal HCl to give 1.52 g (74%) of Compound 8. mp 141–143° C. CIMS m/z 375 (MH+). $^1$H NMR (300 MHz, DMSO-$d_6$) δ 8.2 (Ar, 2H); 8.1–7.95 (Ar, 2H); 7.75–7.5 (Ar, 4H); 6.85 (Ar, 1H); 4.15 (s, 3H); 3.45–3.2 (m, 6H); 2.8 (bq, 2H); 1.7 (m, 5H); 1.85 (m, 1H). Anal calc'd for: $C_{24}H_{26}N_2O_2$.HCl.0.4$H_2O$: Theory: C, 68.94; H,6.70; N, 6.70. Found: C, 69.12; H, 6.55; N, 6.70; KF water 1.63.

Procedure 5

2-Chloro-1-[4-(1-naphthalenoyl)-1-methyl-1H-pyrrol-2-yl]ethanone

A mixture of 4 g (0.025 mole) of (1-methyl-1H-pyrrol-2-yl)-2-chloroethanone, 9.7 g (0.055 mole) of 2-naphthalenoyl chloride and 6.7 g (0.05 mole) of aluminum chloride in 50 mL of 1,2-dichloroethane was heated under reflux for 4 h. The reaction mixture was cooled then poured into 2 N HCl/ice. The organics were separated off, washed with water, $NaHCO_3$, water, brine and dried ($K2CO_3$). The solvent was evaporated in vacuo and the residue chromatographed on silica gel (4:1 hexane:acetone) to give 5.66 g (73%) of 2-chloro-1-[4-(1-naphthalenoyl-1-methyl-1H-pyrrol-2-yl)]ethanone. mp 158–159 ° C. CIMS m/z 312 (MH+). $^1$H NMR (300 MHz, DMSO-$d_6$) δ 8.3 (Ar, 1H); 8.0–7.9 (Ar, 4H); 7.7–7.5 (Ar, 4H); 4.55 (s, 2H); 4.0 (s, 3H).

Using the method of Procedure 5 and the appropriate aroyl chloride, the following compounds were prepared:

2-Chloro-1-[4-(2-thienoyl)-1-methyl-1H-pyrrol-2-yl] ethanone mp 114–116° C. CIMS m/z 268 (MH+). $^1$H NMR (300 MHz, $CDCl_3$) δ 7.8 (Ar, 1H); 7.7 (Ar, 1H); 7.6 (Ar, 2H); 7.2 (Ar 1H); 4.6 (s, 2H); 4.0 (s, 3H).

2-Chloro-1-[4-(2-naphthalenoyl)-1-methyl-1H-pyrrol-2-yl]ethanone

CIMS m/z 312 (MH+). $^1$H NMR (300 MHz, $CDCl_3$) δ 8.15 (Ar, 1H); 8.0 (Ar, 1H); 7.95 (Ar, 1H); 7.7 (Ar, 1H); 7.–7.45 (Ar, 4H); 7.3 (Ar, 1H); 4.5 (s, 2H); 4.0 (s, 3H).

2-Chloro-1-[4-(5-chloro-2-thienoyl)-1-methyl-1H-pyrrol-2-yl)]ethanone mp. 143–145° C. CIMS m/z 302 (MH+). $^1$H NMR (300 MHz, $CDCl_3$) δ 7.6 (Ar, 2H); 7.5 (Ar, 1H); 7.0 (Ar, 1H); 4.6 (s, 2H); 4.0 (s, 3H).

EXAMPLE 8

1-[5-(2-Naphthalenoyl)-1-methyl-1H-pyrrol-3-yl]-2-(N,N-diethylamino)ethanone (Compound 13)

A solution of 2.6 g (0.0084 mole) of 2-chloro-1-[4-(2-naphthalenoyl-1-methyl-1H-pyrrol-2-yl)]ethanone and 5.2 mL (0.050 mole) of diethylamine in 75 mL of EtOH was heated under reflux for 2.5 h. The solvent was evaporated in vacuo. The residue was partitioned between $Et_2O$/3 N NaOH, the organics were separated off, washed with water and brine then dried ($Na_2SO_4$). The solvent was evaporated in vacuo and chromatographed twice on silica gel (90:10:1 $CH_2Cl_2$:MeOH:$NH_4OH$ then 95:5:0.5 $CH_2Cl_2$:MeOH:$NH_4OH$). The residue was treated with ethereal HCl and the solid recrystallized from 2-PrOH to give 0.6 g (19%) of Compound 13. mp 195–196° C. CIMS m/z 349 (MH+). 'H NMR (300 MHz, DMSO-$d_6$) δ 8.5 (Ar, 1H); 8.2–8.05 (Ar, 3H); 7.9 (Ar, 3H); 7.65 (Ar, 2H); 4.85 (d, 2H); 4.0 (s, 3H); 3.2 (m, 4H); 1.3 (t, 6H). Anal calc'd for: $C_{22}H_{24}N_2O_2$.HCl: Theory: C, 68.38; H, 6.55; N, 7.28. Found: C, 68.38; H, 6.35; N, 7.00.

Using the method of Example 8 and the appropriate amine and ethanone, the following compounds were prepared:

EXAMPLE 9

1-[4-(2-Naphthalenoyl)-1-methyl-1H-pyrrol-2-yl]-2-(1-piperidinyl)ethanone (Compound 17)

mp. 246–248° C. CIMS m/z 361 (MH+). $^1$H NMR (300 MHz, DMSO-$d_6$) δ 8.5 (Ar, 1H); 8.2–8.05 (Ar, 3H); 7.9 (Ar, 3H); 7.65 (Ar, 2H); 4.85 (d, 2H); 4.0 (s, 3H); 3.4 (m, 2H); 3.0 (m, 2H);1.9–1.65 (m, 4H); 1.4 (m, 2H). Anal calc'd for: $C_{23}H_{24}N_2O_2$.HCl: C,69.60; H, 6.35; N, 7.06. Found: C, 69.21; H, 6.32; N, 6.29.

EXAMPLE 10

1-[4-(5-Chloro-2-thienoyl)-1-methyl-1H-pyrrol-2-yl]-2-(1-piperidinyl)ethanone (Compound 18)

mp 178–181° C. CIMS m/z 316 (MH+). $^1$H NMR (300 MHz, DMSO-$d_6$) δ 8.25 (Ar, 1H); 8.0 (ar, 1H); 7.8 (Ar, 1H); 7.4 (Ar, 1H); 4.8 (m, 2H); 4.0 (s, 3H); 3.5–3.3 (m, 3H); 3.0 (m, 2H); 1.9–1.6 (m, 5H). Anal calc'd for: $C_{17}H_{19}ClN_2O_2S$.HCl: C, 52.72; H, 5.20; N, 7.23 Found: C, 52.54; H, 5.19; N, 7.12.

EXAMPLE 11

1-[4-(2-Thienoyl)-1-methyl-1H-pyrrol-2-yl]-2-(N,N-diethylamino)ethanone (Compound 2)

mp196–198° C. CIMS m/z 304 (MH+). $^1$H NMR (300 MHz, DMSO-$d_6$) δ 8.2 (Ar, 1H); 8.05 (Ar, 2H); 7.9 (Ar, 1H); 7.4

(t, 1H); 4.8 (d, 2H); 4.0 (s, 3H); 3.25 ( m, 4H); 1.2 (t, 6H). Anal Calc'd for: $C_{16}H_{20}N_2O_2S \cdot HCl$: Theory: C, 56.38; H, 6.21; N, 8.22. Found: C, 56.45; H, 6.16; N, 8.09.

EXAMPLE 12

1-[4-(1-Naphthalenoyl)-1-methyl-1H-pyrrol-2-yl]-2-(N,N-diethylamino)ethanone (Compound 3)

mp. 222–224° C. CIMS m/z 349 (MH$^+$). $^1$H NMR (300 MHz, DMSO-d$_6$) δ 8.15 (Ar, 1H); 8.05 (Ar, 1H); 7.95 (Ar, 1H); 0. 7–7.5 (Ar, 5H); 7.4 (Ar,1H); 4.4 (d, 2H); 4.0 (s, 3H)3.5 (m, 4H); 1.5 (t, 6H). Anal calc'd for: $C_{22}H_{24}N_2O_2 \cdot HCL$: C, 68.65; H, 6.55; N, 7.28. Found: C, 68.52; H, 6.64; N, 6.95.

EXAMPLE 13

1-[4-(1-Naphthalenoyl)-1-methyl-1H-pyrrol-2-yl]-2-(1-piperidinyl)ethanone (Compound 4)

mp 246–248° C. CIMS m/z 361 (MH$^+$). $^1$H NMR (300 MHz, DMSO-d$_6$) δ 8.15 (Ar, 1H); 8.1–8.0 (Ar, 2H); 7.9 (Ar, 1H); 7.8–7.6 (Ar, 5H); 4.8 (d, 2H); 3.95 (s, 3H); 3.4 (bm, 2H); 3.0 (m, 2H); 1.9–1.6 (m, 5H); 1.4 (m, 1H). Anal calc'd for: $C_{23}H_{24}N_2O_2 \cdot HCl$: C, 69.60; H, 6.35; N, 7.06. Found: C, 69.57; H, 6.31; N, 6.62.

Procedure 6

1-[4-(2-Naphthalenoyl)-1H-pyrrol-2-yl]ethanone

A mixture of 7.5 g (0.069 mole) of 2-acetylpyrrole, 17 g (0.089 mole) of 2-naphthalenoyl chloride and 18.3 (0.14 mole) of aluminum chloride in 200 mL of 1,2-dichloroethane was stirred for 4 h and then heated at 65° C. for 1.5 h. After cooling, the reaction mixture was poured into 2N HCl/ice. The organics were separated, washed with water, NaHCO$_3$, water, brine and dried (MgSO$_4$). The solvent was evaporated in vacuo and the residue recrystallized from EtOAc to give 9.25 g (51%) of 1-[4-(2-naphthalenoyl)-1H-pyrrol-2-yl]ethanone. mp 172–174° C. CIMS m/z 264 (MH$^+$). $^1$H NMR (300 MHz, CDCl$_3$) δ 8.4 (Ar, 1H); 8.0–7.9 (Ar, 4H); 7.7–7.55 (Ar, 3H); 7.5 (Ar, 1H); 2.55 (s, 3H).

Procedure 7

3-(2-Naphthalenoyl)-1-[(4-methylphenyl)sulfonyl]-1H-pyrrole

A mixture of 23.0 g (0.11 mole) of tosylpyrrole, 21.25 (0.11 mole) of 2-naphthalenoyl chloride and 27 g (0.22 mole) of aluminum chloride in 350 mL of 1,2-dichloroethane was stirred for 4 h. The reaction mixture was poured into 2 N HCl/ice. The organics were separated, washed with water, NaHCO$_3$, water, brine and dried (Na$_2$SO$_4$). Evaporation of the solvent in vacuo gave 43 g (100%) of 2-(2-naphthalenoyl)-1-[(4-methylphenyl)sulfonyl]-1H-pyrrole. CIMS m/z 376 (MH$^+$). $^1$H NMR (300 MHz, CDCl$_3$) δ 8.4 (Ar, 1H); 8.0–7.9 (Ar, 3H); 7.85–7.75 (Ar, 3H); 7.65–7.5 (Ar, 2H); 7.4–7.2 (Ar, 3H); 6.9 (Ar, 1H); 2.4 (s, 3H).

Procedure 8

3-(2-Naphthalenoyl)-1H-pyrrole

Into a flask was placed 46 g (0.12 mole) of 3-(2-naphthalenoyl)-1-[(4-methylphenyl)sulfonyl]-1H-pyrrole, 250 mL of 1,4-dioxane and 59.8 mL (0.18 mole) of 3 N NaOH. The reaction mixture was stirred overnight after which Et$_2$O and water were added. The organics were separated off, washed with water, brine and dried (Na$_2$SO$_4$). Evaporation of the solvent in vacuo and crystallization from toluene gave 13.5 g of (51%) 3-(2-naphthalenoyl)-1H-pyrrole. mp134–136° C. CIMS m/z 223 (MH$^+$). $^1$H NMR (300 MHz, CDCl$_3$) δ 8.35 (Ar, 1H); 7.9 (Ar, 4H); 7.7 (Ar, 1H); 7.5 (Ar, 2H); 7.4 (Ar, 1H); 6.85 (Ar, 1H).

Procedure 9

2-Chloro-1-[4-(2-naphthalenoyl)-1H-pyrrol-2-yl] ethanone

A mixture of 12.82 g (0.058 mole) of 3-(2-naphthalenoyl)-1H-pyrrole, 7 mL (0.087 mole) of chloroacetyl chloride and 7.7 g (0.12 mole) of aluminum chloride in 500 mL of 1,2-dichloroethane was stirred at room temperature for 1 h. The reaction mixture was heated to reflux for 3 h. Another 7 g of aluminum chloride was added and refluxing continued for 1 h. After cooling, the reaction mixture was poured into 2 N HCl/ice, the organics were separated, washed with water, NaHCO$_3$, water, brine and dried (Na$_2$SO$_4$). The solvent was evaporated in vacuo and recrystallized from toluene to give 13.9 g (81%) of 2-chloro-1-[4-(2-naphthalenoyl)-1H-pyrrol-2-yl]ethanone. mp 175–177° C. CIMS m/z 299 (MH$^+$). $^1$H NMR (300 MHz, CDCl$_3$) δ 8.4 (Ar, 1H); 8.0–7.85 (Ar, 4H); 7.7–7.5 (Ar, 4H); 4.6 (s, 2H).

Procedure 10

1-[4-(2-Naphthalenoyl)-1H-pyrrol-2-yl]-2-(1-piperidinyl)ethanone

A solution of 12.2 g (0.041 mole) of 2-chloro-1-[4-(2-naphthalenoyl)-1H-pyrrol-2-yl]ethanone and 12 mL (0.123 mole) of piperidine in 250 mL of 2-PrOH was heated under reflux for 2 h. The solvent was evaporated in vacuo. The residue was partitioned between Et$_2$O/THF and 3N NaOH, the organics were then washed with water, brine and dried (Na$_2$SO$_4$). The solvent was evaporated in vacuo and the residue passed through a silica column with 90:10:0.5 CH$_2$Cl$_2$:MeOH:NH$_2$OH as eluant to give 14.4 g (100%) of a 1-[4-(2-naphthalenoyl)-1H-pyrrol-2-yl]-2-(1-piperidinyl) ethanone. CIMS m/z 346 (MH$^+$).

EXAMPLE 14

1-[4-(2-Naphthalenoyl)-1-(N,N-dimethylaminoeth-2-yl)-1H-pyrrol-2-yl]-2-(1-piperidinyl)ethanone (Compound 5)

A mixture of 3 g (0.0086 mole) of 1-[4-(2-naphthalenoyl)-1H-pyrrol-2-yl]-2-(1-piperidnyl)ethanone, 1.7 g (0.011 mole) of dimethylaminoethyl chloride, 1.8 g (0.026 mole) of potassium iodide, and 10.8 g (0.082 mole) K$_2$CO$_3$ in 120 mL of DMF was stirred at room temperature overnight. Another 1 g of dimethylaminoethyl chloride and 1 g of potassium iodide were added and the reaction was again stirred overnight. The reaction was poured into water and extracted twice with Et$_2$O. The organics were washed with water, brine and dried (Na$_2$SO$_4$). The solvent was evaporated in vacuo. The resulting oil was twice chromatographed on silica gel (90:10:1 CH$_2$Cl$_2$:MeOH:NH$_2$OH) and converted to the HCl salt with ethereal HCl to give 0.94 g of Compound 5 (26%). mp 239–242° C. CIMS m/z 418 (MH$^+$). $^1$H NMR (300 MHz, Me$_2$SO$_4$-d$_6$) δ 8.6 (Ar, 1H); 8.3 (Ar, 1H); 8.2 (Ar, 1H); 8.05 (Ar, 2H); 7.9 (Ar, 2H); 7.7 (Ar, 2H); 4.8 (m, 4H); 3.55 (m, 4H); 3.4 (s, 6H); 3.1 (m, 3H); 1.9 (m, 3H); 1.7 (m, 3H); 1.5 (m, 1H). Anal calc'd for: $C_{26}H_{31}$, $N_3O_2 \cdot HCl \cdot 0.4H_2O$: C, 62.73; H, 6.85; N, 8.44. Found: C, 62.67; H, 6.80; N, 8.25. KF water 1.5%.

Procedure 11

[(4-Chlorophenyl)-1-ethyl methoxy-1H-pyrrol-2-yl] methanone

A solution of 4.8 mL (0.062 mole) of potassium t-butoxide 1.0M in THF added dropwise to 10 g (0.048 mole) of (4-chlorophenyl)-1H-pyrrol-2-ylmethanone in 60 mL of THF. After stirring for 20 minutes, a solution of 5.6 mL (0.062 mole) of chloroethylmethyl ether in 40 mL of THF was added dropwise. The reaction mixture was refluxed for 72 h after which 5 mL of chloroethylmethyl ether was added and refluxing continued overnight. Another 5 mL of chloroethylmethyl ether was added with an additional 24 h of refluxing. The reaction was poured into water and extracted with $Et_2O$. The organics were washed with water, brine and dried ($MgSO_4$). The solvent was evaporated in vacuo to give 10.5 g (83%) of [(4-chlorophenyl)-1-ethylmethoxy-1H-pyrrol-2-yl]methanone. CIMS m/z 264 ($MH^+$). $^1H$ NMR (300 MHz, $CDCl_3$) δ 7.75 (d, 2H); 7.45 (d, 2H); 7.1 (Ar, 1H); 6.75 (Ar, 1H) 6.2 (Ar, 1H) 4.6 (t, 2H); 3.75 (t, 2H); 3.3 (s, 3H).

Procedure 12

2-Chloro-1-[5-(4-chlorobenzoyl)-1-ethylmethoxy-1H-pyrrol-3-yl]ethanone

A mixture of 9.27 g (0.035 mole) of [(4-chlorophenyl)-1-ethylmethoxy-1H-pyrrol-2-yl]methanone, 11 g (0.086 mole) of aluminum chloride, and 6.5 mL (0.07 mole) of chloroacetyl chloride in 50 mL of 1,2-dichloroethane was stirred overnight. The reaction mixture was poured into 2 N HCl/ice, the organics were washed with $NaHCO_3$, water, brine and dried ($MgSO_4$). The solvent was evaporated in vacuo and the residue chromatographed on silica gel (5:1 hexane:acetone) to give 9 g (100%) of 2-chloro-1-[5-(4-chlorobenzoyl)-1-ethylmethoxy-1H-pyrrol-3-yl]ethanone. CIMS m/z 340 ($MH^+$). $^1H$ NMR (300 MHz, $CDCl_3$) δ 7.8 (Ar, 3H) 7.45 (Ar, 2H); 7.2 (Ar, 1H); 4.6 (t, 2H); 4.5 (s, 2H); 3.75 (t, 2H); 3.3 (s, 3H).

EXAMPLE 15

1-[5-(4-Chlorobenzoyl)-1-ethylmethoxy-1H-pyrrol-3-yl]2-[N,N-diethylamino]ethanone (Compound 9)

A solution of 3.19 g (0.0094 mole) of 2-chloro-1-[5-(4-chlorobenzoyl)-1-ethylmethoxy-1H-pyrrol-3-yl]ethanone, 75 mL of 2-PrOH, and 2.9 mL (0.028 mole) of diethylamine was heated under reflux for 4 h. The solvent was evaporated in vacuo. The residue was partitioned between $Et_2O$ and 2N NaOH. The organics were washed with water, brine and dried ($Na_2SO_4$). The solvent was evaporated in vacuo and the residue chromatographed on silica gel (9:1 $CH_2Cl_2$: MeOH). The oil was treated with ethereal HCl and the resulting solid recrystallized from 2-PrOH to give 0.9 g (26%) of Compound 9. mp 149–151° C. CIMS m/z 377 (MH+). $^1H$ NMR (300 MHz, DMSO-$d_6$) δ 8.2 (Ar, 1H); 7.8 (Ar, 2H); 7.7 (Ar, 2H); 7.2 (Ar, 1H); 4.7 (m, 2H); 4.6 (t, 2H); 3.65 (t, 2H); 3.2 (m, 3H); 3.15 (m, 4H); 1.2 (t, 6H). Calc'd for: $C_{20}H_{25}ClN_2O_3 \cdot HCl$: C, 5.12; H, 634; N, 6.78. Found: C, 58.29; H, 6.31; N, 6.55.

EXAMPLE 16

1-[5-(4-Chlorobenzoyl)-1-(N,N-dimethylaminoprop-3-yl)-1H-pyrrol-3-yl]-2-(1-piperidinyl)ethanone (Compound 14)

A solution of 2 g (0.006 mole) of 1-[5-(4-chlorobenzoyl)-1H-pyrrol-3-yl]-2-(1-piperidinyl)ethanone, 1.4 g (0.0078 mole) of dimethylaminopropyl chloride hydrochloride, 5.2 g (0.042 mole) of $K_2CO_3$, and 1 g (0.006 mole) of potassium iodide in 40 mL of DMF was stirred overnight then heated to 70° C. for 5 h. After cooling the reaction mixture was poured into water, and extracted with $Et_2O$. The organics were washed with water, brine and dried ($K_2CO_3$). The solvent was evaporated in vacuo and treated with ethereal HCl in 2-PrOH to give 0.73 g (29%) of Compound 14. mp 138–141° C. CIMS m/z416 (MH+). $^1H$ NMR (300 MHz, DMSO-$d_6$) δ 8.35 (Ar, 1H); 7.8 (Ar, 2H); 7.7 (Ar, 2H); 7.2 (Ar, 1H); 4.8 (m, 2H); 4.6 (t, 2H); 3.4 (m, 3H); 3.15–2.9 (m, 4H); 2.75 (d, 6H); 2.2 (m, 2H); 1.9–1.65 (m, 4H); 1.4 (m, 1H). Anal calc'd for: $C_{23}H_{30}ClN_3O_2 \cdot 2HCl \cdot 1.3H_2O$: C, 54.00; H, 6.80; N, 8.21. Found: C, 53.69; H, 6.89; N, 7.93 KF 4.04.

EXAMPLE 17

1-[5-(4-Chlorobenzoyl)-1-methyl-1H-pyrrol-3-yl]-2-(4-methyl-1-piperazinyl)ethanone (Compound 7)

Using the procedure of Example 1 and the appropriate chloroketone and amine, Compound 7 was prepared. mp. 237–239° C. CIMS m/z=350 ($MH^+$). $^1HNMR$ (300 MHz, DMSO-$d_6$) δ 8.2 (Ar, 1H); 7.8 (Ar, 2H); 7.6 (Ar, 2H); 7.2 (Ar, 1H); 4.45 (bs, 2H); 4.0 (s, 4H); 3.4 (bs, 1H); 2.95 (bs, 2H); 2.5 (m, 3H); 1.2 (t, 4H). Anal calc'd for: $C_{19}H_{22}ClN_3O_2 \cdot HCl \cdot 0.65H_2O$: C, 51.34; H, 5.74; N, 9.45. Found: C, 51.12; H, 5.86; N, 9.36.

Procedure 13

2-Chloro-1-[5-(4-Chlorobenzoyl)-1H-pyrrol-3-yl]ethanone.

Using the 2-benzoyl-pyrroles described in U.S. Pat. No. 5,512,537 to Tsang (hereby incorporated by reference) as starting materials, the method of Procedure 9 and substituting (2-chlorophenyl)-1H-pyrrol-3-ylmethanone, the title compound was prepared. CIMS m/z =283 ($MH^+$). $^1HNMR$ (300 MHz, $CDCl_3$) δ 7.9 (Ar, 1H); 7.6–7.3 (Ar, 4H); 7.0 (Ar, 1H); 4.45 (s, 2H).

Procedure 14

1-[5-(2-Chlorobenzoyl)-1H-pyrrol-3-yl]-2-(N,N-diethylamino)ethanone

Using the method of Procedure 10 and substituting 2-chloro-1-[5-(4-chlorobenzoyl)-1H-pyrrol-3-yl]ethanone and N,N-diethylamine, the title compound was prepared. CIMS m/z= 319 ($MH^+$). $^1HNMR$ (300 MHz, $CDCl_3$) δ 8.0 (Ar, 1H); 7.55–7.3 (Ar, 4H); 7.1 (Ar, 1H); 3.7 (s, 2H); 2.7 (q, 4H); 1.1 (t, 6H).

EXAMPLE 18

1-[5-(2-Chlorobenzoyl)-1-ethylthiomethyl-1H-pyrrol-3-yl]-2-(N,N-diethylamino)ethanone (Compound 16)

0.2 g (0.0045 moles) of 60% NaH in oil was washed with hexane and 3 mL of DMF was added. To the suspension was added a solution dropwise of 1.2 g (0.0035 moles) of 1-[5-(2-chlorobenzoyl)-1H-pyrrol-3-yl]-2-(N,N-diethylamino)ethanone in 8 mL of DMF. After stirring for 10 m, 1.5 mL (0.0070 moles) of chloroethyl methyl sulfide was added and the reaction heated to 65° C. for 4 h. Water was added and extracted with $Et_2O$, the organics were washed with water, brine and dried ($Na_2SO_4$). The solvent was evaporated in vacuo. The resulting oil was passed through a Biotage Flash 40 L, silica gel (97:3:0.1 $CH_2Cl_2$:MeOH:$NH_4OH$), then treated with ethereal HCl. After recrystallizing from 2-PrOH, 0.11 g of Compound 16; mp 157–158° C. CIMS m/z=393 (MH+). $^1HNMR$ (300 MHz, DMSO-$d_6$) δ 8.3 (Ar, 1H); 7.6–7.4 (Ar, 4H); 6.9 (Ar, 1H); 4.7 (m, 4H); 3.3(s,3H); 3.2 (m, 4H); 2.9 (m, 2H); 1.2 (t, 6H). Anal calc'd for $C_{20}H_{25}ClN_2O_2S \cdot HCl$: C, 55.94; H, 6.1; N, 6.52. Found: C, 55.77, H, 6.12; N, 6.31.

BIOLOGICAL EXAMPLES

The compounds of the present invention are useful as agents for the treatment of central nervous system disorders. The following biological examples demonstrate the use of the instant compounds in a method for the treatment of central nervous system disorders including, but not limited to, use as anticonvulsants, antiepileptics, neuroprotective agents, muscle relaxants and as agents for the treatment of neuropathic pain.

Procedure for Testing in Mouse Anticonvulsant Model

The compounds of Formula (I) and Formula (II) are useful as anticonvulsant agents. The anticonvulsant activity of the subject compounds was determined using a standard "maximal electroshock test" (MES). In this test, activity is indicated by a block of the toxic extensor seizure, as described by Swinyard, et al., in *J. PharmacoL Exptl. Therap.*, 106, 319 (1952). A more recent description of current anticonvulsant drug screening is given in Swinyard, et al., in *Epilepsia*, 19, 409 (1978).

The anticonvulsant activity of compounds of this invention tested according to the Swinyard (1952) method are shown in Table 3, having values for the Mouse MES Model in $ED_{50}$ per dose (in mg/kg, i.p.).

Procedure for Testing in a Neuropathic Pain Model

The compounds of the present invention are useful in the treatment of neuropathic pain. The use of the compounds in treating neuropathic pain was determined using an animal model. This model was developed and first described by S. H. Chung and J. M. Chung, An Experimental Model for Peripheral Neuropathy Produced by Segmental Spinal Nerve Ligation in the Rat, *Pain*, 1992, 50, 355–363 (referred to hereinafter as the "Chung Model").

Male Sprague-Dawley rats, weighing approximately 200 g each were anesthetized with isoflurane. The spinal nerve at the level of $L_5$ was exposed through an incision just left of the dorsal midline and tightly ligated with 6-0 silk. At various times after surgery, animals were tested for mechanical allodynia with von Frey hairs (monofilaments which are calibrated to bend under a certain amount of pressure, ranging from 0.41 to 15.1 g). In order to calculate a paw withdrawal threshold (PWT), tactile allodynia was measured by recording the pressure at which the affected paw was withdrawn from graded stimuli according to the procedure of S. R. Chaplan, J. W. Pogrel, T. L. Yaksh, Role of Voltage-Dependent Calcium Channel Subtypes in Experimental Tactile Allodynia, *J. Pharmacol. Exp. Ther.* 1994, 269,1117–1123. Normal rats can withstand at least 15 g of pressure without responding. Operated rats, however, can respond to as little as 0.25 g of pressure. The surgery was deemed successful if the animal responded with a PWT of less than 4 g of pressure applied to the affected paw.

The sham operation consisted of a similar surgery; the spinal nerve was visualized without being ligated. These animals were also tested for mechanical allodynia and showed no response to greater than 15 g of force applied to the ipsilateral paw. The results of the assay were expressed as percent of the maximum possible effect (% MPE), calculated as the PWT at the time of testing minus the baseline PWT divided by the maximum PWT (15 g) minus the baseline PWT times 100.

The compounds having Formula (I) and Formula (II) were tested for activity against neuropathic pain by being dissolved or suspended in either water or hydroxypropyl methylcellulose, respectively. Postoperative animals between 14 to 42 days were fasted overnight prior to dosing. Animals were orally dosed and dosage volumes were calculated on a 4 mL/kg basis. The screening dose employed was 30 mg/kg. Table 3 also shows the antiallodynic activity in % MPE for solutions of compounds of the present invention.

TABLE 3

| Cpd | MES $ED_{50}$ | % MPE |
|---|---|---|
| 1 | 10.98 | 80 |
| 2 | Active @ 30 | 14 |
| 3 | Active @ 30 | 87 |
| 4 | Active @ 30 | 12 |
| 5 | Active @ 300 | 15 |
| 6 | Active @ 30 | 54 |
| 7 | 16.6 | 21 |
| 8 | Active @ 30 | 25 |
| 9 | Active @ 100 | 5 |
| 10 | Active @ 100 | 0 |
| 11 | Active @ 30 | 34 |
| 12 | Active @ 100 | 4 |
| 13 | Active @ 300 | 80 |
| 14 | Active @ 300 | 71 |
| 15 | Active @ 30 | 40 |

For treating epilepsy, a compound having Formula (I) and Formula (II) may be employed at a daily dosage in the range of about 30 to 2000 mg, usually in 2 to 4 divided doses, for an average adult human. A unit dose would contain about 10 to 500 mg of the active ingredient.

In general, a compound having Formula (I) and Formula (II) may be used in treating epilepsy in a manner similar to that used for phenytoin. Medical aspects of the treatment of epilepsy are described in L. S. Goodman, et. Al., in "The Pharmacological Basis of Therapeutics", 5th Ed. pages 201 to 226, Macmillan (1975).

The results of the "Chung Model" study are statistically significant and suggest that the compounds of the present invention are also effective in reducing neuropathic pain. For treating neuropathic pain, a compound having Formula (I) and Formula (II) may be employed at a daily dosage in the range of about 30 to 2000 mg, usually in 2 to 4 divided doses, for an average adult human. A unit dose would contain about 10 to 500 mg of the active ingredient. More generally, for mammals, the treatment would comprise the daily administration of from about 0.5 mg/kg to about 50 mg/kg.

To prepare the pharmaceutical compositions of this invention, one or more compounds having Formula (I) or Formula (II) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of the active ingredient.

The foregoing compositions are particularly suitable for use in the treatment of epilepsy or the symptoms of epilepsy by a method comprising internally administering to a subject suffering from the symptoms of epilepsy compositions comprising an effective epilepsy inhibiting amount of a compound having Formula (I) and Formula (II).

What is claimed is:

1. A compound having Formula (I) and Formula (II):

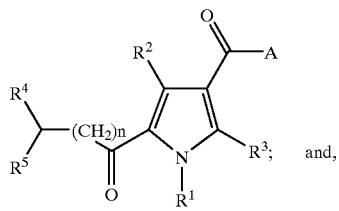

Formula (I)

and,

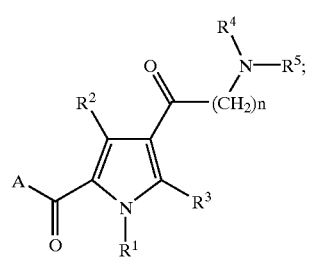

Formula (II)

wherein

A is a substituent selected from the group consisting of aryl and heteroaryl optionally substituted with one to two substituents selected from the group consisting of halogen, $C_{1-8}$alkyl, $C_{1-8}$alkoxy, tri(halogen)$C_{1-8}$alkyl and tri(halogen)$C_{1-8}$alkoxy;

n is an integer from 1 to 5;

$R^1$ is $C_{1-8}$alkyl optionally substituted with one to two substituents independently selected from the group consisting of hydroxy, $C_{1-8}$alkoxy (optionally substituted with —$SC_{1-8}$alkyl), $C_{1-8}$acyl, carboxy, carbonyl (further substituted with $C_{1-8}$alkyl, $C_{1-8}$alkoxy, amino or —$SC_{1-8}$alkyl), oxy (further substituted with carbonyl$C_{1-8}$alkyl, carbonyl$C_{1-8}$alkoxy or carbonylamino), amino (optionally further substituted with one or two substituents independently selected from $C_{1-8}$alkyl, $C_{1-8}$acyl, carbonyl$C_{1-8}$alkyl, carbonyl$C_{1-8}$alkoxy, sulfinyl$C_{1-8}$alkyl or sulfonyl$C_{1-8}$alkyl), ureido (optionally further substituted with $C_{1-8}$alkyl), thio (optionally further substituted with $C_{1-8}$alkyl or amino), sulfinyl (optionally further substituted with $C_{1-8}$alkyl or amino) and sulfonyl (optionally further substituted with $C_{1-8}$alkyl or amino);

$R^2$ and $R^3$ are substituents independently selected from the group consisting of hydrogen and $C_{1-8}$alkyl;

$R^4$ and $R^5$ are substituents independently selected from the group consisting of hydrogen, $C_{1-8}$alkyl and aryl$C_{1-8}$alkyl; wherein aryl is optionally substituted with one to three substituents selected from the group consisting of $C_{1-8}$alkyl, $C_{1-8}$alkoxy, tri(halo)$C_{1-8}$alkyl and tri(halo)$C_{1-8}$alkoxy;

or, in the alternative, $R^4$ and $R^5$ may be fused together with nitrogen to form a heterocyclic ring selected from the group consisting of:

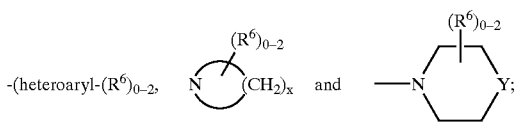

wherein x is an integer from 3 to 7 and Y is selected from the group consisting of N, S, S=O, $SO_2$ and O; and $R^6$ is a substituent selected from the group consisting of $C_{1-8}$alkyl and hydroxy$C_{1-8}$alkyl;

and pharmaceutically acceptable acid addition salts thereof; with the proviso that, in the case of a compound wherein:

n is an integer from 1 to 5; $R^1$ is selected from the group consisting of hydrogen and $C_{1-4}$alkyl; $R^2$ and $R^3$ are selected from the group consisting of hydrogen and $C_{1-4}$alkyl; $R^4$ and $R^5$ are independently selected from the group consisting of hydrogen, $C_{1-4}$alkyl, phenyl$C_{1-4}$alkyl and substituted phenyl$C_{1-4}$alkyl where the substituent is on phenyl and selected from the group consisting of methyl and methoxy; or in the alternative, are fused and together with the nitrogen form a heterocyclic ring selected from the group consisting of: 4-[bis(4-fluorophenyl)methylene]-piperidin-1-yl, 1,2,3,4-tetrahydro-6,7-dimethoxy-isoquinolin-2-yl,

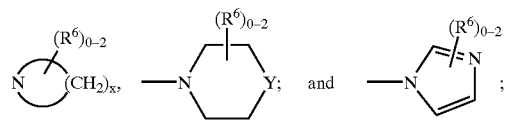

wherein Y is S or O and x is 3 to 7; and, $R^6$ is selected from the group consisting of methyl and hydroxymethyl;

then, A cannot be substituted or unsubstituted phenyl.

2. The compound of claim 1 selected from the group consisting of

1-[4-(2-Naphthalenoyl)-1-methyl-1H-pyrrol-2-yl]-2-(N, N-diethylamino)ethanone;

1-[4-(2-Thienoyl)-1-methyl-1H-pyrrol-2-yl]-2-(N,N-diethylamino)ethanone;

1-[4-(1-Naphthalenoyl)-1-methyl-1H-pyrrol-2-yl]-2-(N, N-diethylamino)ethanone;

1-[4-(1-Naphthalenoyl)-1-methyl-1H-pyrrol-2-yl]-2-(1-piperidinyl)ethanone;

1-[4-(2-Naphthalenoyl)-1-(N,N-dimethylaminoeth-2-yl)-1H-pyrrol-2-yl]-2-(1-piperidinyl)ethanone;

1-[5-(5-Chlorothieno-2-yl)-1-methyl-1H-pyrrol-3-yl]-2-(N,N-diethylamino)ethanone;

1-[5-(4-Chlorobenzoyl)-1-methyl-1H-pyrrol-3-yl]-2-(4-methyl-1-piperazinyl)ethanone;

1-[5-(1-Naphthalenoyl)-1-methyl-1H-pyrrol-3-yl]-3-(1-piperidinyl)-1-propanone;

1-[5-(4-Chlorobenzoyl)-1-ethylmethoxy-1H-pyrrol-3-yl]-2-[N, N-diethylamino]ethanone;

1-[5-(2-Thienoyl)-1-methyl-1H-pyrrol-3-yl]-2-(N,N-diethylamino)ethanone;

1-[5-(2-Thienoyl)-1-methyl-1H-pyrrol-3-yl]-2-(1-piperidinyl)ethanone;

1-[5-(3-Pyridinoyl)-1-methyl-1H-pyrrol-3-yl]-2-(N, N-diethylamino)ethanone;

1-[5-(2-Naphthalenoyl)-1-methyl-1H-pyrrol-3-yl]-2-(N, N-diethylamino)ethanone;

1-[5-(4-Chlorobenzoyl)-1-(N, N-dimethylaminoprop-3-yl)-1H-pyrrol-3-yl]-2-(1-piperidinyl)ethanone;
1-[5-(2-Naphthalenoyl)-1-methyl-1H-pyrrol-3-yl]-2-(N, N-ethylmethylamine)ethanone;
1-[5-(2-Chlorobenzoyl)-1-ethylthiomethyl-1H-pyrrol-3-yl]-2-(N,N-diethylamino)ethanone;
1-[4-(2-Naphthalenoyl)-1-methyl-1H-pyrrol-2-yl]-2-(1-piperidinyl)ethanone; and,
1-[4-(5-Chloro-2-thienoyl)-1-methyl-1H-pyrrol-2-yl]-2-(1-piperidinyl)ethanone;

and pharmaceutically acceptable acid addition salts thereof.

3. The compound of claim 1 having Formula (I), selected from the group consisting of

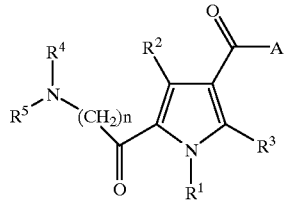

Formula (I)
wherein n, A, $R^1$, $R^2$, $R^3$, $R^4$ and $R^5$ are selected from

| n | A | $R^1$ | $R^2/R^3$ | $R^4/R^5$ |
|---|---|---|---|---|
| 1 | 2-naphthalenyl | $CH_3$ | H/H | $CH_2CH_3/CH_2CH_3$; |
| 1 | 2-thienyl | $CH_3$ | H/H | $CH_2CH_3/CH_2CH_3$; |
| 1 | 1-naphthalenyl | $CH_3$ | H/H | $CH_2CH_3/CH_2CH_3$; |
| 1 | 1-naphthalenyl | $CH_3$ | H/H | 1-piperidinyl; |
| 1 | 2-naphthalenyl | $(CH_2)_2N(CH_3)_2$ | H/H | 1-piperidinyl; |
| 1 | 2-naphthalenyl | $CH_3$ | H/H | 1-piperidinyl; and, |
| 1 | 2-(5-Cl)thienyl | $CH_3$ | H/H | 1-piperidinyl; | and pharmaceutically acceptable acid addition salts thereof.

4. The compound of claim 1 having Formula (II), selected from the group consisting of

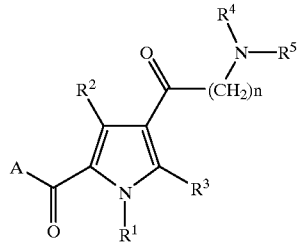

Formula (II)
wherein n, A, $R^1$, $R^2$, $R^3$, $R^4$ and $R^5$ are selected from

| n | A | $R^1$ | $R^2/R^3$ | $R^4/R^5$ |
|---|---|---|---|---|
| 1 | 2-(5-Cl)thienyl | $CH_3$ | H/H | $CH_2CH_3/CH_2CH_3$; |
| 1 | 4-Cl—Ph | $CH_3$ | H/H | 4-$CH_3$-1-piperazinyl; |
| 2 | 1-naphthalenyl | $CH_3$ | H/H | 1-piperidinyl; |
| 1 | 4-Cl—Ph | $(CH_2)_2OCH_3$ | H/H | $CH_2CH_3/CH_2CH_3$; |
| 1 | 2-thienyl | $CH_3$ | H/H | $CH_2CH_3/CH_2CH_3$; |
| 1 | 2-thienyl | $CH_3$ | H/H | 1-piperidinyl; |
| 1 | 3-pyridinyl | $CH_3$ | H/H | $CH_2CH_3/CH_2CH_3$; |
| 1 | 2-naphthalenyl | $CH_3$ | H/H | $CH_2CH_3/CH_2CH_3$; |
| 1 | 4-Cl—Ph | $(CH_2)_3N(CH_3)_2$ | H/H | 1-piperidinyl; |
| 1 | 2-naphthalenyl | $CH_3$ | H/H | $CH_3/CH_2CH_3$; and, |
| 1 | 2-Cl—Ph | $(CH_2)_2SCH_3$ | H/H | $CH_2CH_3/CH_2CH_3$; | and pharmaceutically acceptable salts thereof.

5. A method for the treatment of neuropathic pain comprising the step of administering to a mammal suffering from such disorder a therapeutically effective amount of the compound of claim 1.

6. The method of claim 5 wherein the therapeutically effective amount of the compound of claim 1 is from about 0.5 mg/kg/day to about 50 mg/kg/day.

* * * * *